United States Patent
Tokura

(10) Patent No.: US 12,138,022 B2
(45) Date of Patent: Nov. 12, 2024

(54) SPHYGMOMANOMETER USING LASER DOPPLER FLOWMETER, PHOTOPLETHYSMOGRAM, AND HEART RATE MONITOR

(71) Applicant: Nippon Telegraph and Telephone Corporation, Tokyo (JP)

(72) Inventor: Akio Tokura, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 309 days.

(21) Appl. No.: 17/629,238

(22) PCT Filed: Aug. 8, 2019

(86) PCT No.: PCT/JP2019/031393
§ 371 (c)(1),
(2) Date: Jan. 21, 2022

(87) PCT Pub. No.: WO2021/024460
PCT Pub. Date: Feb. 11, 2021

(65) Prior Publication Data
US 2022/0265158 A1 Aug. 25, 2022

(51) Int. Cl.
*A61B 5/021* (2006.01)
*A61B 5/00* (2006.01)
(Continued)

(52) U.S. Cl.
CPC ...... *A61B 5/02125* (2013.01); *A61B 5/02427* (2013.01); *A61B 5/0245* (2013.01);
(Continued)

(58) Field of Classification Search
CPC .................................................. A61B 5/681
See application file for complete search history.

(56) References Cited

U.S. PATENT DOCUMENTS 6,176,832 B1    1/2001  Habu et al.
2003/0109791 A1*  6/2003  Kondo ............... A61B 5/021
                                              600/500
(Continued)

FOREIGN PATENT DOCUMENTS

CA    2466012 A1 *  5/2003
JP    H1176233 A    3/1999
(Continued)

OTHER PUBLICATIONS

M. Nitzan et al, "Automatic noninvasive measurement of systolic blood pressure using photoplethysmography", BioMedical Engineering OnLine, vol. 8, No. 28, pp. 1-8, Oct. 2009 (Year: 2009).*
(Continued)

*Primary Examiner* — Joel Lamprecht
*Assistant Examiner* — Nyrobi Celestine
(74) *Attorney, Agent, or Firm* — Slater Matsil, LLP

(57) ABSTRACT

An embodiment optical blood pressure monitor includes a laser Doppler blood flowmeter, which measures the blood flow velocity in a peripheral blood vessel, a photoplethysmography monitor, which measures the pulse waveform in a peripheral blood vessel, a heart rate monitor, which measures data relating to the pulsation of a heart, a characteristic point extraction portion, which extracts a characteristic point relating to the pulsation from the data relating to the pulsation of the heart, a first calculation portion, which determines the pulse wave velocity from the pulse waveform, and a second calculation portion, which determines the blood pressure based on the pulse wave velocity and the blood flow velocity.

17 Claims, 9 Drawing Sheets

(51) Int. Cl.
  *A61B 5/024* (2006.01)
  *A61B 5/0245* (2006.01)
  *A61B 5/026* (2006.01)
  *A61B 7/04* (2006.01)
(52) U.S. Cl.
  CPC ............ *A61B 5/0261* (2013.01); *A61B 5/681* (2013.01); *A61B 5/7278* (2013.01); *A61B 7/04* (2013.01)

(56) References Cited

U.S. PATENT DOCUMENTS

| | | | |
|---|---|---|---|
| 2004/0030261 A1* | 2/2004 | Rantala | A61B 5/0285 600/561 |
| 2011/0054277 A1* | 3/2011 | Pinter | A61B 5/02125 600/529 |
| 2016/0270708 A1 | 9/2016 | Tateda et al. | |
| 2016/0353998 A1* | 12/2016 | Lee | A61B 5/6824 |
| 2017/0095171 A1* | 4/2017 | Park | A61B 5/02007 |
| 2017/0172510 A1* | 6/2017 | Homyk | A61B 5/721 |
| 2017/0238817 A1* | 8/2017 | Lading | A61B 5/6824 |
| 2017/0251936 A1* | 9/2017 | Sawado | A61B 8/4227 |
| 2018/0192896 A1 | 7/2018 | Kato et al. | |
| 2019/0209030 A1 | 7/2019 | Shimuta | |

FOREIGN PATENT DOCUMENTS

| | | | |
|---|---|---|---|
| JP | 2014217707 A | | 11/2014 |
| JP | 2017127494 A | * | 7/2017 |
| JP | 2019058345 A | | 4/2019 |
| WO | 2015049963 A1 | | 4/2015 |
| WO | 2017047541 A1 | | 3/2017 |
| WO | 2018030380 A1 | | 2/2018 |

OTHER PUBLICATIONS

JP-2017127494-A (Year: 2017).*
K. Meigas et al, "Continuous Blood Pressure Monitoring Using Pulse Wave Delay", 2001 Proceedings of the 23rd Annual EMBS International Conference, pp. 3171-3174, Oct. 2001 (Year: 2001).*
J. Hagblad et al, "A technique based on laser Doppler flowmetry and photoplethysmography for simultaneously monitoring blood flow at different tissue depths", Medical and Biological Engineering and Computing, vol. 48, pp. 415-422, Jan. 2010 (Year: 2010).*
Z. Abdollahi et al, "Evaluation of a combined reflectance photoplethysmography and laser Doppler flowmetry surface probe", 35th Annual International Conference of the IEEE EMBS, pp. 1728-1731, Jul. 2013 (Year: 2013).*
Takazawa, K. et al., "Assessment of Vasoactive Agents and Vascular Aging by the Second Derivative of Photoplethysmogram Waveform," American Heart Association, Inc., vol. 32, No. 2, Jan. 24, 1998, 6 pages.
Watanabe, N. et al., "Development and Validation of a Novel Cuff-Less Blood Pressure Monitoring Device," JACC: Basic to Translational Science, vol. 2, No. 6, Dec. 2017, 12 pages.

* cited by examiner

SPHYGMOMANOMETER USING LASER DOPPLER FLOWMETER, PHOTOPLETHYSMOGRAM, AND HEART RATE MONITOR

This patent application is a national phase filing under section 371 of PCT application no. PCT/JP2019/031393, filed on Aug. 8, 2019, which application is hereby incorporated herein by reference.

TECHNICAL FIELD

The present invention relates to a blood pressure monitor.

BACKGROUND

The majority of conventional blood pressure monitors widely used at home and for medical purposes use the oscillometric method. With such a conventional blood pressure monitor, a cuff (arm band) is wrapped around the user's upper arm or the like, and the pressure pulse wave is measured while pressurizing or decompressing through the cuff. The systolic blood pressure (maximum blood pressure) and diastolic blood pressure (minimum blood pressure) are determined from the characteristic points of the pulse wave.

In general, the oscillometric method has a high affinity with fully automatic measurement and digital measurement. As such, many products of conventional blood pressure monitors are highly convenient, and the pressurization and decompression through the cuff, measurement and calculation of blood pressure, and digital display of the result are automatically performed when the user wraps the cuff around an arm and presses the measurement button.

However, conventional blood pressure monitors that use the oscillometric method require pressurization and decompression through the cuffs. This makes it difficult to measure blood pressure in situations where pressure stimulation is not desired, such as when the user is sleeping or relaxing.

For this reason, optical blood pressure monitors using optical measurement have been studied as blood pressure monitors that do not involve the pressurization of the user's arm or the like (see NPL 1 and NPL 2).

A prominent optical blood pressure measurement technique applies incoherent light to a peripheral blood vessel using an LED or the like, detects the reflected or transmitted light with a light receiving element, and uses the pulse waveform in the blood vessel obtained from the variation in the amount of received light. When light of a specific wavelength that is absorbed by erythrocyte hemoglobin and the like is applied to a peripheral blood vessel, the amount of light that is not absorbed and detected by the light receiving element reflects changes in the blood volume in the blood vessel, that is, vascular volume. Thus, based on the amount of light detected by the light receiving element, a pulse waveform (hereinafter, also referred to as "photoplethysmography") is obtained. This type of measurement method is referred to as photoplethysmophram.

CITATION LIST

Non Patent Literature

[NPL 1] Takazawa, Kenji et al. "Assessment of vasoactive agents and vascular aging by the second derivative of photoplethysmogram waveform" Hypertension 32 2 (1998): 365-70.

[NPL 2] Watanabe, Naoki et al. "Development and Validation of a Novel Cuff-Less Blood Pressure Monitoring Device" JACC. Basic to translational science (2017).

SUMMARY

Technical Problem

However, since a conventional optical blood pressure monitor obtains the variation in the blood pressure based only on photoplethysmogram, it may be difficult to measure the blood pressure accurately, for example, when the user's vascular movement is small. In particular, in patients with advanced arteriosclerosis or calcification of blood vessels due to diseases such as diabetes, blood pressure measurement may be difficult due to small vascular movement.

To solve the above problem, it is an objective of embodiments of the present invention to provide a blood pressure monitor that accurately measures blood pressure.

Means for Solving the Problem

In order to solve the above-mentioned problems, a blood pressure monitor according to embodiments of the present invention includes: a first measuring instrument configured to measure a blood flow velocity in a peripheral blood vessel; a second measuring instrument configured to measure a pulse waveform in a peripheral blood vessel; a third measuring instrument configured to measure data relating to pulsation of a heart; a characteristic point extraction portion configured to extract a characteristic point relating to the pulsation from the data relating to the pulsation of the heart; a first calculation portion configured to determine a pulse wave velocity from the pulse waveform using the characteristic point; and a second calculation portion configured to determine blood pressure based on the pulse wave velocity and the blood flow velocity.

Effects of Embodiments of the Invention

According to embodiments of the present invention, the pulse wave velocity is determined from the pulse waveform in a peripheral blood vessel using characteristic points extracted from data relating to the pulsation of the heart, and blood pressure is determined based on the pulse wave velocity and the blood flow velocity in the peripheral blood vessel. This increases the accuracy of blood pressure measurement.

DETAILED DESCRIPTION OF ILLUSTRATIVE EMBODIMENTS

Referring to FIGS. 1 to 18, preferred embodiments of the present invention are now described in detail.

Summary of Embodiments of the Invention

The blood pressure monitor according to embodiments of the present invention is an optical blood pressure monitor 1 that uses optical measurement. The outline of the optical blood pressure monitor 1 according to the present embodiment is now described.

The relationship between the blood pressure variation and pulse waves can be expressed as follows (see Reference 1).

Expression (1)

$$C^2 = \Delta P/\rho \cdot (V/\Delta V) \quad (1)$$

Here, C denotes pulse wave velocity, P denotes blood pressure, ρ denotes blood density, V denotes blood vessel volume, and Δ denotes variation amount.

Expression (1) can be written as Expression (2) below through expansion using a relation $V=\rho L (D/2)^2$, where L denotes the length of the blood vessel and D denotes the diameter of the blood vessel.

Expression (2)

$$C^2 = \Delta P/2\rho \cdot (D/\Delta D) \quad (2)$$

Since the variation in blood density ρ is often not large, blood pressure (blood pressure variation) can be determined when the pulse wave velocity C and the relation [V/ΔV] or the relation [D/ΔD] are known. For example, the above-mentioned conventional example uses pulse waveforms (photoplethysmogram) to determine the pulse wave velocity C and the relation [V/ΔV] or the relation [D/ΔD] (see NPL 1 and NPL 2).

Here, the pulse wave velocity C represented by Expressions (1) and (2) is relatively easy to determine. However, when the user is a patient with extremely advanced arteriosclerosis or calcification due to diabetes, for example, the vascular movement is relatively small. In such a case, when only photoplethysmogram is used, it becomes difficult to accurately detect the relation [V/ΔV] or the relation [D/ΔD].

For example, diabetic patients often have impaired renal function and may require dialysis. Since dialysis is a long process, patients may sleep during dialysis. As such, continuous blood pressure monitoring is desired that monitors for a sudden decrease in blood pressure while the patient is undergoing dialysis without involving pressurizing so as not to interfere with the patient's rest. However, in some cases, accurate blood pressure monitoring cannot be achieved by conventional optical blood pressure measurement that uses only photoplethysmogram.

Figure 1:
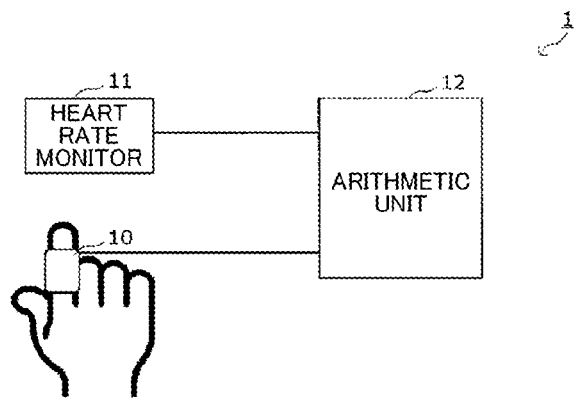
FIG. 1 is a block diagram showing the configuration of an optical blood pressure monitor according to an embodiment of the present invention.
Figure 6:
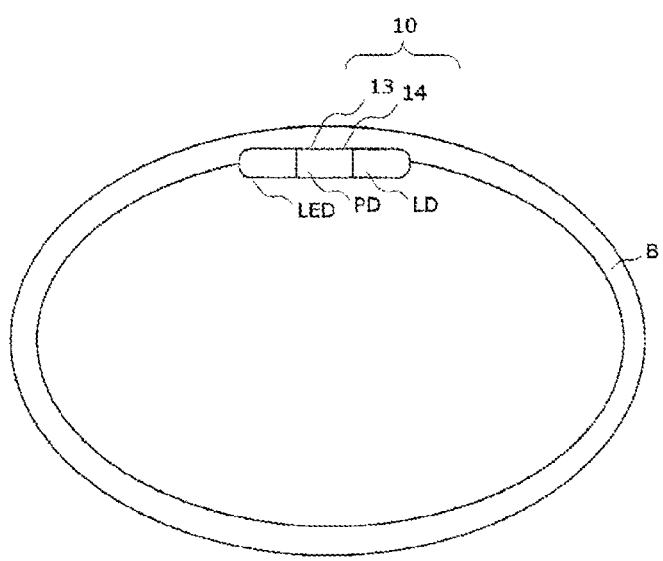
FIG. 6 is a schematic view of an optical sensor device according to a first embodiment as viewed from a side.

As shown in FIG. 1, the optical blood pressure monitor 1 according to the present embodiment includes an optical sensor device 10 to be placed on a user's finger or the like, a heart rate monitor (third measuring instrument) ii for measuring the electrocardiographic waveform of the user, and an arithmetic unit 12. As shown in FIG. 6, the optical sensor device 10 includes a laser Doppler blood flowmeter (first measuring instrument) 13 and a photoplethysmography monitor (second measuring instrument) 14.

The laser Doppler blood flowmeter 13 is a device that measures the blood flow of a capillary vessel near the surface of the user's skin using coherent light. The blood flow rate and blood flow velocity are determined using the Doppler effect, in which the frequency of the scattered light resulting from the light applied to a moving object changes according to the moving speed of the object.

In the blood flow measurement by laser Doppler measurement, when Q denotes blood flow rate, f denotes the frequency of the scattered light, and p denotes the power spectrum of the light-receiving signal at the frequency f, the blood flow rate Q is expressed by the following Expression (3).

Expression (3)

$$Q = \Sigma fp \quad (3)$$

When blood volume is BV, blood volume BV can be given by Σp, so the blood flow velocity U is given by the following Expression (4).

Expression (4)

$$U = Q/BV = \Sigma fp/\Sigma p \quad (4)$$

As for the relationship between the relation [D/ΔD] for the diameter of the blood vessel of Expression (2) described above and blood flow measurement, the dilation of a blood vessel increases the cross-sectional area of the blood vessel and reduces the blood flow velocity U, and the constriction of the blood vessel reduces the cross-sectional area of the blood vessel and increases the blood flow velocity U. Here, the relation [D/ΔD] can be replaced with the relation [−2U/ΔU] including blood flow velocity U.

The relationship between the blood pressure variation and the pulse wave of the above-mentioned Expression (2) is expressed by the following Expression (5).

Expression (5)

$$C^2 \propto \Delta P/\rho \cdot (U/\Delta U) \qquad (5)$$

Expression (5) can be rewritten as the following Expression (6), where k denotes proportionality constant.

Expression (6)

$$\Delta P = k \cdot \rho C^2 \cdot (\Delta U/U) \qquad (6)$$

Blood flow measurement using laser Doppler measurement is accurate but may have limited time responsiveness because a large amount of data needs to be Fourier transformed when determining measurement values. For this reason, the optical blood pressure monitor 1 according to the present embodiment determines the pulse wave velocity C with the photoplethysmography monitor 14 that uses photoplethysmography.

To determine the pulse wave velocity C, the difference in propagation time of pulse waves is measured, and an electrocardiographic waveform or a phonocardiographic waveform, for example, may be used as a starting point. FIGS. 2 to 5 are schematic views showing the relationship between an electrocardiographic waveform (a), a phonocardiographic waveform (b), and a pulse waveform (c).

Figure 2:
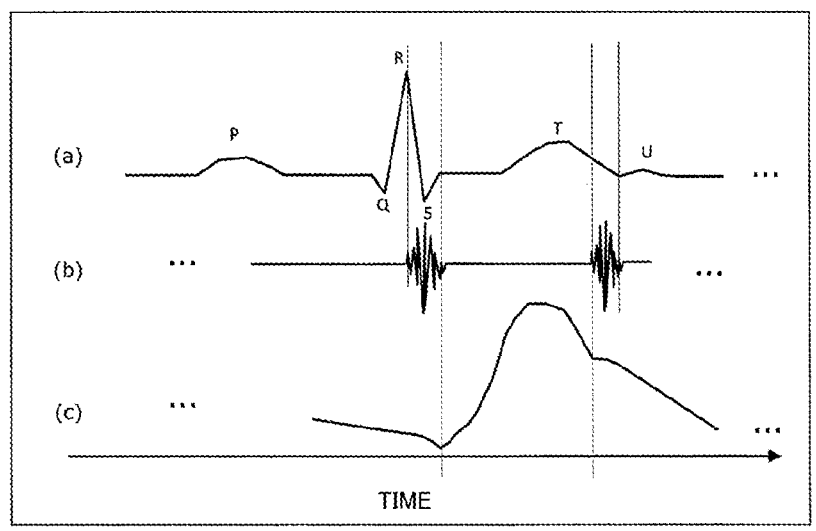
FIG. 2 is a diagram illustrating the outline of an optical blood pressure monitor according to an embodiment of the present invention.

As shown in FIG. 2, Sound I of the phonocardiographic waveform (b) occurs between the peak of the R wave and the ST junction of the electrocardiographic waveform (a). Also, Sound II is generated in the phonocardiographic waveform (b) between T and U of the electrocardiographic waveform (a). In the present embodiment, for example, the start time point of the ST junction is used as the starting point, that is, a characteristic point.

Figure 3:
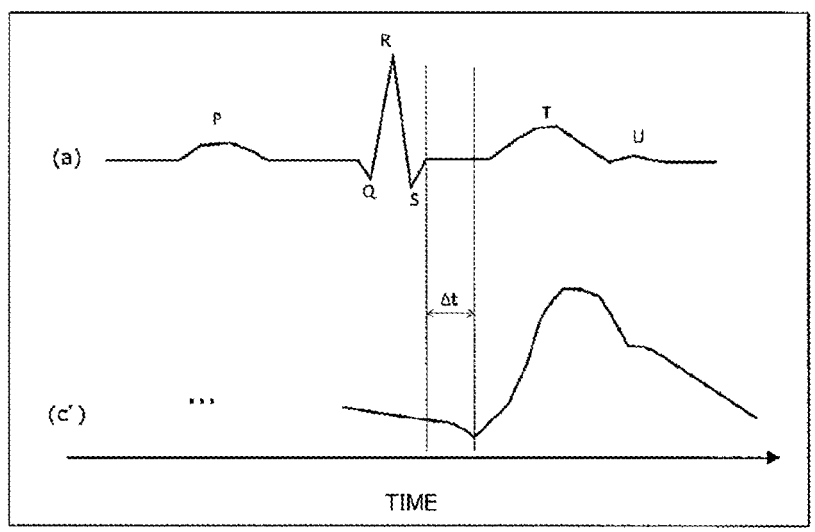
FIG. 3 is a diagram illustrating the outline of an optical blood pressure monitor according to an embodiment of the present invention.
Figure 4:
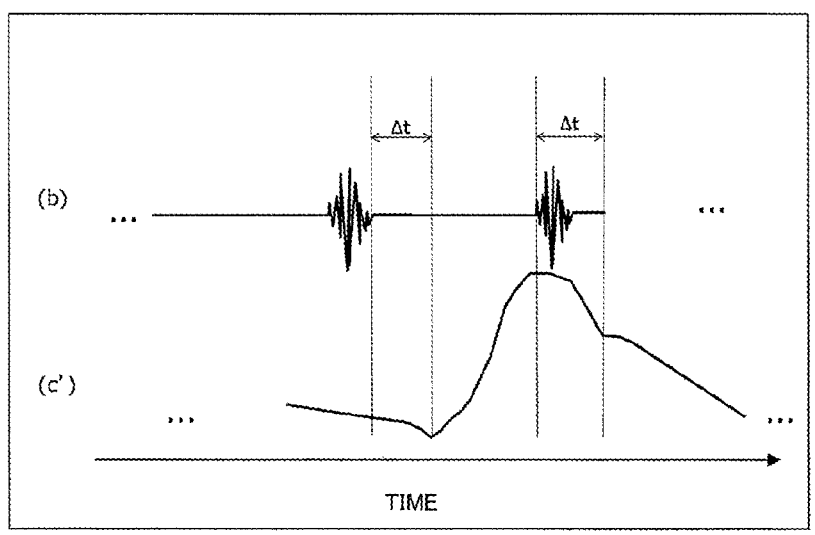
FIG. 4 is a diagram illustrating the outline of an optical blood pressure monitor according to an embodiment of the present invention.

In the pulse waveform (c) shown in FIG. 2, the time point of the characteristic point of the pulse waveform (c) extracted based on at least one of the electrocardiographic waveform (a) and the phonocardiographic waveform (b) is used as the reference, and the pulse wave transit time is determined based on the time point difference Δt from the time point of the characteristic point of the pulse waveform (c') shown in FIG. 3. FIG. 3 shows an example in which the characteristic point of the pulse waveform (c) is extracted based on the electrocardiographic waveform (a). FIG. 4 shows an example in which the characteristic point of the pulse waveform (c) is extracted based on the phonocardiographic waveform (b).

Figure 5:
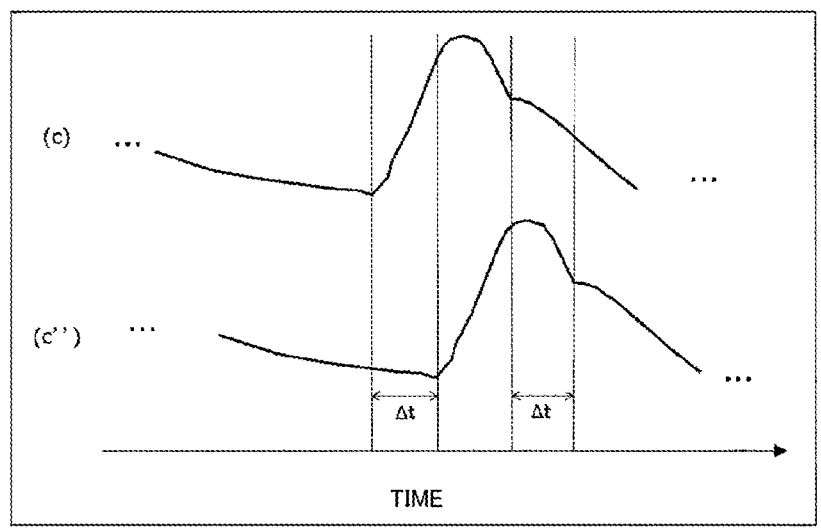
FIG. 5 is a diagram illustrating the outline of an optical blood pressure monitor according to an embodiment of the present invention.

In the example of FIG. 4, the time points corresponding to the end time of Sound I and the start time of Sound II are used as the characteristic points of the pulse waveform (c). As shown in FIG. 5, instead of using the electrocardiographic waveform (a) or the phonocardiographic waveform (b), the time point difference Δt of the characteristic points may be determined by comparing pulse waveforms (c) and (c″) in two locations at certain distances from the heart.

When the time point difference Δt between the characteristic points in pulse waveforms is thus determined and the blood vessel length for pulse wave propagation is fixed, that is, the measurement location is fixed, the pulse wave velocity C can be determined from the reciprocal of the propagation time.

The calculation of the blood pressure involves the measurement of the blood density ρ. However, changes in the blood density ρ are small as compared to the other parameters in Expression (6), so that the blood density ρ can be considered constant in the course of measurement. As such, blood pressure and blood pressure variation can be accurately measured by calibrating the measurement value (blood pressure value) and determining the values of blood density ρ and proportionality constant k before starting measurement with the optical blood pressure monitor 1 of the present embodiment.

As described above, one of the features of the optical blood pressure monitor 1 according to the present embodiment is that it determines blood pressure based on the blood flow velocity U measured using laser Doppler measurement and the pulse wave velocity C determined from pulse waveforms measured using photoplethysmography.

First Embodiment

Referring to FIGS. 1 to 13, an optical blood pressure monitor 1 according to the present embodiment is now described.

As shown in FIG. 1, the optical blood pressure monitor 1 includes an optical sensor device 10, a heart rate monitor 11, and an arithmetic unit 12. The present embodiment uses an electrocardiograph as the heart rate monitor 11 to obtain data relating to the pulsation of the heart of the user. As shown in FIGS. 1 and 6, the optical sensor device 10 is provided in a ring-type wearable terminal attached to a user's finger.

Configuration of Optical Sensor Device

Figure 7:
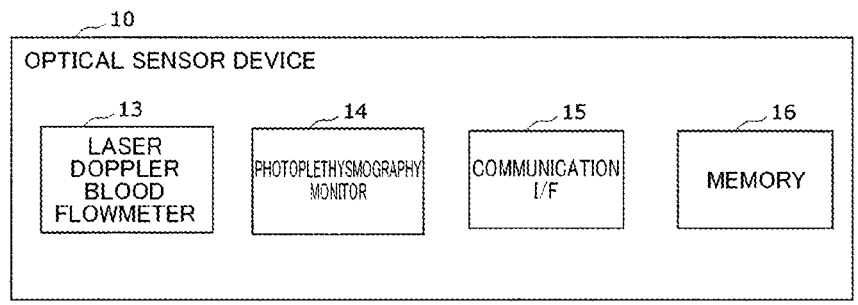
FIG. 7 is a block diagram showing the configuration of the optical sensor device according to the first embodiment.

As shown in FIG. 7, the optical sensor device 10 includes a laser Doppler blood flowmeter 13, a photoplethysmography monitor 14, a communication interface (I/F) 15, and a memory 16.

FIG. 6 is a schematic view of the optical sensor device 10 as viewed from a side. The optical sensor device 10 is provided in a ring member B. As shown in FIG. 6, the ring member B is formed in a tubular shape. Specifically, in FIG. 6, the laser Doppler blood flowmeter 13 and the photoplethysmography monitor 14 are provided on the side of the ring member B that corresponds to the palmar side of the user's finger. As shown in FIG. 6, in the present embodiment, the laser Doppler blood flowmeter 13 and the photoplethysmography monitor 14 are integrally formed.

The ring member B can be formed in a band shape with fabric or the like. For example, it can be fixed around a user's finger by a hook-and-loop fastener. Alternatively, it can be configured to be fixed around a user's finger with a material such as elastic fabric. In this case, the laser Doppler blood flowmeter 13 and the photoplethysmography monitor 14 may be fixed to the side of the band-shaped ring member B corresponding to the palmar side of the user's finger with an adhesive or the like.

In another example, the ring member B may be made of a synthetic resin, such as plastic or elastomer, ora non-magnetic metal, such as aluminum or stainless steel. In this case, a recess may be formed in the ring member B, and the laser Doppler blood flowmeter 13 and the photoplethysmography monitor 14 may be fitted into the recess.

The communication I/F 15 and the memory 16 of the optical sensor device 10 are now described.

The communication I/F 15 is a communication control circuit for communicating with various external electronic devices via a communication network NW. The data measured by the laser Doppler blood flowmeter 13 and the photoplethysmography monitor 14 is transmitted from the communication I/F 15 to the arithmetic unit 12, which will be described below, via the communication network NW.

The communication I/F 15 may include a communication interface circuit and an antenna compatible with wireless data communication standards or wired data communication standards such as Bluetooth (registered trademark), Bluetooth Low Energy, LTE, 3G, 4G, 5G, wireless LAN, and the like.

The memory 16 may be a semiconductor memory, for example. The memory 16 pre-stores a program used by a calculation portion 33 of the laser Doppler blood flowmeter 13, which will be described below, and a calculation portion 43 of the photoplethysmography monitor 14 to perform various controls and operations. The memory 16 also has an area for recording the calibration data for the laser Doppler blood flowmeter 13 and the photoplethysmography monitor 14.

Configuration of Laser Doppler Blood Flowmeter

Figure 8:
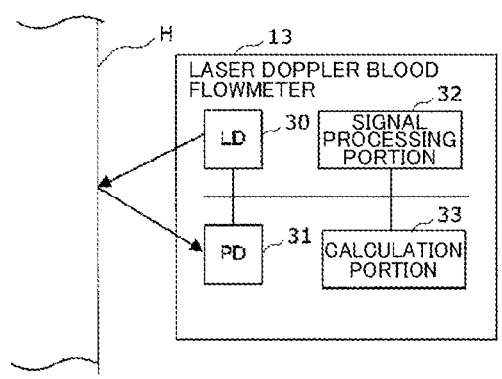
FIG. 8 is a block diagram showing the configuration of a Doppler blood flowmeter according to the first embodiment.

As shown in FIGS. 6 and 8, the laser Doppler blood flowmeter 13 includes a semiconductor laser (first light source) LD 30, a photodiode (first light receiving element) PD 31, a signal processing portion 32, and a calculation portion 33.

As indicated by arrows in FIG. 8, the LD 30 emits coherent light toward the blood flowing through a peripheral blood vessel near the user's skin surface H. In the present embodiment, a light source that emits a laser beam having an infrared wavelength is used as the LD 30.

The PD 31 receives scattered light generated when the coherent light is applied to the blood and converts it into an electric signal by photoelectric conversion.

The signal processing portion 32 converts the analog electric signal into a digital signal by amplifying the electric signal output from the PD 31, removing noises by filtering, and using a predetermined sampling frequency. The signal processing portion 32 includes an amplifier circuit, a filter, and an AD converter, for example.

The calculation portion 33 includes a processor such as an MPU. The calculation portion 33 determines the blood flow velocity in the peripheral blood vessel based on the digital signal of the scattered light obtained by the signal processing portion 32. Specifically, the calculation portion 33 calculates the blood flow rate Q and the blood volume BV using Expression (3) and calculates the blood flow velocity U using Expression (4). The blood flow velocity determined by the calculation portion 33 is transmitted from the communication I/F 15 to the arithmetic unit 12 via the communication network NW.

The laser Doppler blood flowmeter 13, which includes a sensor drive control circuit (not shown), controls the light emission of the LD 30 and supplies a synchronization signal indicating the light emission timing of the LD 30 to the signal processing portion 32.

Configuration of Photoplethysmography Monitor

Figure 9:
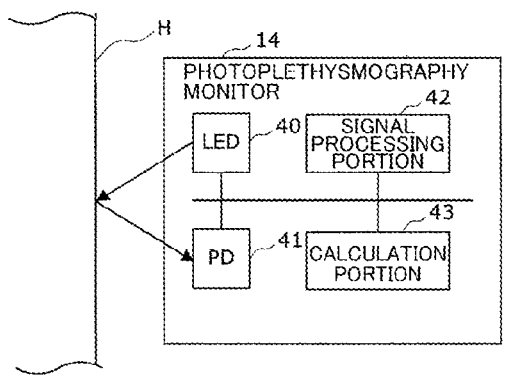
FIG. 9 is a block diagram showing the configuration of a photoplethysmography monitor according to the first embodiment.

As shown in FIG. 9, the photoplethysmography monitor 14 includes an LED (second light source) 40, a photodiode (second light receiving element) PD 41, a signal processing portion 42, and a calculation portion 43, for example.

As indicated by arrows in FIG. 9, the LED 40 emits incoherent light toward the blood flowing through a peripheral blood vessel near the user's skin surface H. In the present embodiment, the LED 40 is a light source that emits light having a visible light wavelength.

The PD 41 receives reflected light or scattered light generated when the incoherent light is applied to the blood, or receives transmitted light when the PD 41 is in a transmission measurement arrangement, and converts it into an electric signal by photoelectric conversion. In the present embodiment, as shown in FIG. 6, the laser Doppler blood flowmeter 13 and the photoplethysmography monitor 14 are integrally formed and provided in the ring member B. In this case, the PD 41 may be shared by the laser Doppler blood flowmeter 13 and the photoplethysmography monitor 14.

When optical measurement cannot be performed simultaneously since one PD is shared by the laser Doppler blood flowmeter 13 and the photoplethysmography monitor 14, the sensors may be configured to perform optical measurement with a set time difference.

The signal processing portion 42, which has the same configuration as the signal processing portion 32, amplifies, filters, and AD-converts the electric signal obtained by the PD 41, and outputs a digital signal representing the reflected light, scattered light, or transmitted light.

The calculation portion 43 includes a processor such as an MPU in the same manner as the calculation portion 33 described above. The calculation portion 43 determines a pulse waveform from the fluctuation amount or the like of the digital signal representing the reflected light or the like obtained by the signal processing portion 42. The pulse waveform in the peripheral blood vessel determined by the calculation portion 43 is transmitted from the communication I/F 15 to the arithmetic unit 12 via the communication network NW. The calculation portion 43 may share the common processor with the calculation portion 33 of the laser Doppler blood flowmeter 13.

The photoplethysmography monitor 14, which includes a sensor drive control circuit (not shown), controls the light emission of the LED 40 and supplies a synchronization signal indicating the light emission timing of the LED 40 to the signal processing portion 42.

The photoplethysmography monitor 14 may use either of transmission measurement and reflection measurement. When the photoplethysmography monitor 14 of transmission measurement is used, it is preferable to use a fingertip or earlobe where the light from the LED 40 can easily pass through the tissue of the living body.

Heart Rate Monitor Configuration

Figure 10:
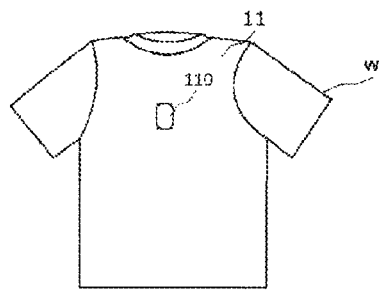
FIG. 10 is a schematic external view showing the configuration of an electrocardiograph according to the first embodiment.

The heart rate monitor 11 according to the present embodiment is now described. As shown in FIG. 10, the heart rate monitor 11 may be a shirt-type wearable device W. The wearable device W has a configuration in which a piece of fabric having a conductive polymer coating on its fiber surface is arranged on a shirt. When the wearable device W having such textile bioelectrodes is worn by the user and comes into contact with the skin surface of the user, the electrocardiographic waveform of the user is measured.

The heart rate monitor 11 includes a transmitter no and transmits the measured electrocardiographic waveform of the user to the arithmetic unit 12, which will be described below, via the communication network NW. Although not shown, the transmitter 110 includes a control board, which may include a communication I/F circuit compatible with communication standards such as Bluetooth (registered trademark) and Bluetooth Low Energy, a memory, an arithmetic circuit, and the like, and a battery. The heart rate monitor 11 is not limited to wireless communication and may communicate with the arithmetic unit 12 by wire.

Functional Block of Arithmetic Unit

Figure 11:
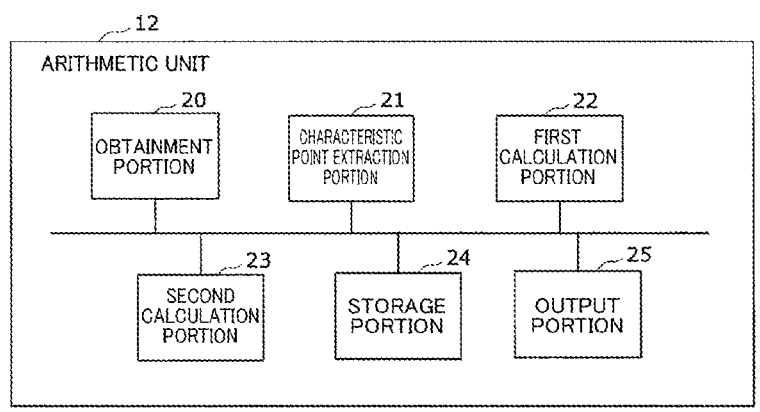
FIG. 11 is a block diagram showing the functional configuration of an arithmetic unit according to the first embodiment.

Referring to the block diagram of FIG. 11, the functional configuration of the arithmetic unit 12 is now described.

As shown in FIG. 11, in one example, the arithmetic unit 12 includes an obtainment portion 20, a characteristic point extraction portion 21, a first calculation portion 22, a second calculation portion 23, a storage portion 24, and an output portion 25.

The obtainment portion 20 obtains the data measured by each of the optical sensor device 10 and the heart rate monitor 11 by wireless or wired communication. Specifically, the obtainment portion 20 obtains a blood flow velocity from the laser Doppler blood flowmeter 13. Further, the obtainment portion 20 obtains a pulse waveform from the photoplethysmography monitor 14. The obtainment portion 20 also obtains an electrocardiographic waveform from the heart rate monitor 11. The storage portion 24 stores the data obtained by the obtainment portion 20.

The characteristic point extraction portion 21 extracts characteristic points relating to the heartbeat from the user's electrocardiographic waveform measured by the heart rate monitor 11. Specifically, as shown in FIGS. 2 and 3, the characteristic point extraction portion 21 may extract the start time point of the ST junction of the electrocardiographic waveform (a) as the starting point, that is, as a characteristic point.

Using the characteristic point of the electrocardiographic waveform extracted by the characteristic point extraction portion 21, the first calculation portion 22 determines the pulse wave velocity from the pulse waveform measured by the photoplethysmography monitor 14. Specifically, as shown in FIG. 3, the first calculation portion 22 determines the pulse wave transit time from the time point difference Δt of the corresponding time point in the pulse waveform, using the start time point of the ST junction of the electrocardiographic waveform as the starting point. Furthermore, the first calculation portion 22 determines the pulse wave velocity from the reciprocal of the pulse wave transit time, with the blood vessel length for pulse wave propagation being fixed. The obtained pulse wave velocity is held in the storage portion 24.

The second calculation portion 23 determines the blood pressure based on the pulse wave velocity and the blood flow velocity measured by the laser Doppler blood flowmeter 13. Specifically, the second calculation portion 23 determines the blood pressure (blood pressure variation) ΔP by substituting the pulse wave velocity C, the blood flow velocity U, and the blood density p and the proportionality constant k determined in advance, using Expression (6) described above.

The storage portion 24 stores the data obtained by the obtainment portion 20 from the optical sensor device 10 and the heart rate monitor 11. The storage portion 24 also stores the characteristic point relating to the heartbeat extracted by the characteristic point extraction portion 21, the pulse wave velocity determined by the first calculation portion 22, and the blood pressure determined by the second calculation portion 23. Furthermore, the storage portion 24 stores the above-mentioned Expression (6) for determining the blood pressure.

The output portion 25 outputs the blood pressure (blood pressure variation) determined by the second calculation portion 23. For example, the output portion 25 can display the blood pressure value on a display device 108 described below. The output portion 25 can also transmit the determined blood pressure value to an external communication terminal device (not shown) or the like.

Hardware Configuration of Arithmetic Unit

Figure 12:
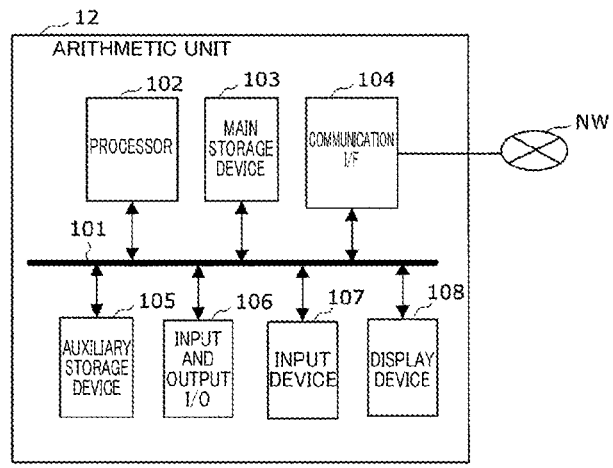
FIG. 12 is a block diagram showing an example of the hardware configuration of the arithmetic unit according to the first embodiment.

Referring to the block diagram of FIG. 12, an example of the hardware configuration of the arithmetic unit 12 having the above-mentioned functions is now described.

As shown in FIG. 12, the arithmetic unit 12 may be formed by a computer including a processor 102, a main storage device 103, a communication I/F 104, an auxiliary storage device 105, an input and output I/O 106, an input device 107, and a display device 108, which are connected via a bus 101, and a program that controls these hardware resources.

The main storage device 103 may be a semiconductor memory such as SRAM, DRAM, or ROM. The main storage device 13 pre-stores a program used by the processor 102 to perform various controls and operations. The processor 102 and the main storage device 103 enable the various functions of the arithmetic unit 12 including the characteristic point extraction portion 21, the first calculation portion 22, and the second calculation portion 23 shown in FIG. 11.

The communication I/F 104 is an interface circuit for communicating with various external electronic devices via a communication network NW. The arithmetic unit 12 receives the data measured by the optical sensor device 10 and the heart rate monitor 11 via the communication I/F 104. The communication I/F 104 forms the obtainment portion 20 shown in FIG. 11.

The communication I/F 104 may include an interface and an antenna compatible with wireless data communication standards such as LTE, 3G, 4G, 5G, wireless LAN, Bluetooth (registered trademark), and Bluetooth Low Energy. Examples of the communication network NW include a wide area network (WAN), a local area network (LAN), the Internet, a dedicated line, a wireless base station, and a provider. The communication I/F 104 may also have a communication control circuit for performing wire communication.

The auxiliary storage device 105 includes a readable and writable storage medium and a drive device for reading and writing various types of information, such as programs and data, to and from the storage medium. A semiconductor memory, such as a hard disk or a flash memory, can be used as the storage medium of the auxiliary storage device 105. The auxiliary storage device 105 forms the storage portion 24 described with reference to FIG. 11.

The auxiliary storage device 105 has a program storage area for storing a program that is used by the arithmetic unit 12 to perform a characteristic point extraction process, pulse wave velocity calculation, and blood pressure calculation. The auxiliary storage device 105 stores information on Expression (6) for determining blood pressure. The auxiliary storage device 105 may also include a backup area for backing up the data and programs described above, for example.

The input and output I/O 106 includes an I/O terminal, which inputs a sign an external device and outputs a signal to an external device.

The input device 107 may include a keyboard and a touch panel and generates and outputs a signal corresponding to key entry or a touch device. For example, the input device 107 can receive input of pre-measured blood pressure values (calibration values) in order to determine blood density p and proportionality constant k.

The display device 108 has a display screen such as a liquid crystal display. The display device 108 forms the output portion 25 described with reference to FIG. 11.

The arithmetic unit 12 does not have to be formed by a single computer, and may be dispersed in multiple computers connected to one another via the communication network NW.

The processor 102 may be hardware such as a field-programmable gate array (FPGA), a large-scale integration (LSI), or an application-specific integrated circuit (ASIC).

Operation of Optical Blood Pressure Monitor

Figure 13:
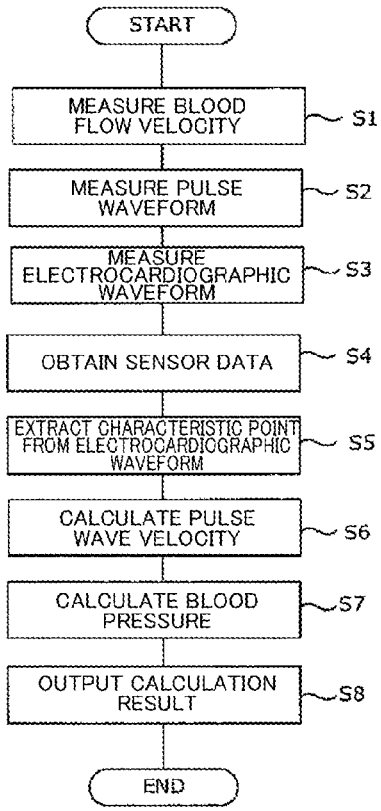
FIG. 13 is a flowchart illustrating the operation of the optical blood pressure monitor according to the first embodiment.

Referring to the flowchart of FIG. 13, the operation of the optical blood pressure monitor 1 having the above-described configuration is now described. In the example described below, it is assumed that the blood pressure value is calibrated in advance using a blood pressure monitor of a pressurization method such as the oscillometric method, and that the blood density ρ and the proportionality constant k are already obtained.

The following process is performed with the user already wearing a shirt-type wearable device W equipped with an electrocardiograph as the heart rate monitor 11 and with the optical sensor device 10 in a ring-type wearable terminal attached to a finger.

First, the laser Doppler blood flowmeter 13 measures the blood flow velocity in a peripheral blood vessel of the user's finger (step S1). The photoplethysmography monitor 14 then measures the pulse waveform in the peripheral blood vessel of the user's finger (step S2). Then, the heart rate monitor 11 measures the electrocardiographic waveform of the user (step S3). Step S2 and step S3 may be performed simultaneously.

Then, the obtainment portion 20 obtains the blood flow velocity, the pulse waveform, and the electrocardiographic waveform measured at steps S1, S2, and S3 (step S4). The characteristic point extraction portion 21 then extracts a characteristic point relating to the heartbeat from the electrocardiographic waveform (step S5). For example, the characteristic point extraction portion 21 may extract the start time point of the ST junction of the electrocardiographic waveform as a characteristic point.

Then, the first calculation portion 22 calculates the pulse wave velocity from the pulse waveform, using the time point of the pulse waveform corresponding to the characteristic point of the electrocardiographic waveform extracted at step S5 as the starting point (step S6). The second calculation portion 23 then calculates the blood pressure (blood pressure variation) by substituting the pulse wave velocity C calculated at step S6, the blood flow velocity in the peripheral blood vessel, and the blood density p and the proportionality constant k determined in advance into Expression (6) (step S7).

Then, the output portion 25 displays the obtained blood pressure value, for example, on the display device 108 (step S8).

As described above, according to the optical blood pressure monitor 1 of the first embodiment, the pulse wave velocity is determined from the pulse waveform using a characteristic point of the electrocardiographic waveform, and the blood pressure is calculated based on the pulse wave velocity and the blood flow velocity in the peripheral blood vessel, achieving blood pressure measurement that is more accurate than the measurement performed based only on photoplethysmogram.

Additionally, since the optical blood pressure monitor 1 of the first embodiment can accurately measure blood pressure without pressurizing the user's body parts such as an arm, it can perform accurate blood pressure measurement for a user with small blood vessel movements due to arteriosclerosis, for example.

Moreover, the optical blood pressure monitor 1 according to the first embodiment can monitor blood pressure variation without pressurization in a situation in which blood pressure measurement of a pressurization method is not desirable, for example when the user is receiving dialysis.

The optical blood pressure monitor 1 according to the first embodiment allows the optical sensor device 10 to be smaller since the laser Doppler blood flowmeter 13 and the photoplethysmography monitor 14 are integrally formed and provided in the ring member B.

The embodiment described above is an example in which the heart rate monitor 11 is the shirt-type wearable device W with wearable electrodes. However, the heart rate monitor 11 may be a 12-lead (12-channel) electrocardiograph (ECG) or an electrocardiograph with patch electrodes, for example.

Modification of First Embodiment

Figure 14:
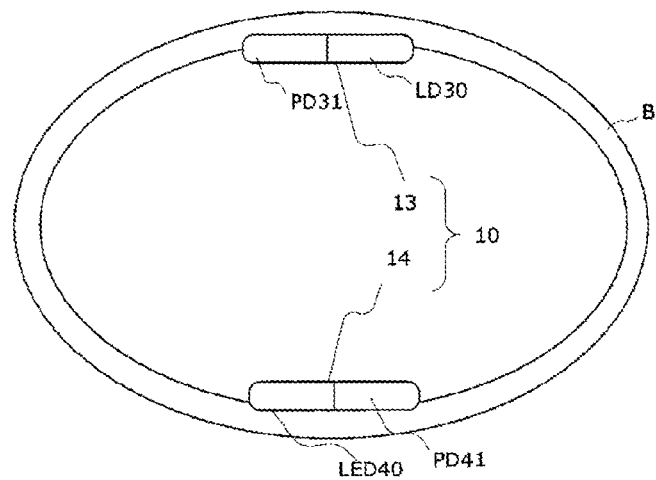
FIG. 14 is a schematic view of an optical sensor device according to a modification of the first embodiment as viewed from a side.

Referring to FIG. 14, a modification of the first embodiment is now described.

FIG. 14 is a schematic view of an optical sensor device 10 according to a modification as viewed from a side. In the first embodiment described above, the laser Doppler blood flowmeter 13 and the photoplethysmography monitor 14 of the optical sensor device 10 are integrally provided in the ring member B. In contrast, in this modification, the laser Doppler blood flowmeter 13 and the photoplethysmography monitor 14 are separately provided in the ring member B.

Specifically, the laser Doppler blood flowmeter 13 is provided on the side of the ring member B that corresponds to the palmar side of the user's finger. When the laser Doppler blood flowmeter 13 is placed on the side corresponding to the palmar side of the finger where the capillary density is higher, the laser Doppler measurement can be performed easily and accurately.

The photoplethysmography monitor 14 is provided on the side of the ring member B corresponding to the dorsal side of the user's finger. For example, the laser Doppler blood flowmeter 13 and the photoplethysmography monitor 14 have PD 31 and PD 41, respectively.

When the transmission photoplethysmography monitor 14 is used, one common PD 31 can be used instead of the separated PD 31 and PD 41.

The configuration in which the laser Doppler blood flowmeter 13 and the photoplethysmography monitor 14 are provided separately in the ring member B still achieves accurate blood pressure measurement in the same manner as the first embodiment.

Second Embodiment

A second embodiment of the present invention is now described. Same reference numerals are given to those configurations that are the same as the corresponding configurations of the first embodiment described above. Such configurations will not be described in detail.

In the first embodiment, the optical sensor device 10 is provided in the ring-type wearable terminal. In contrast, in the second embodiment, the optical sensor device 10 is provided in a wristband-type wearable terminal. Also, as the heart rate monitor 11, a phonocardiography sensor nA is used. The following descriptions focus on the configurations differing from those of the first embodiment.

Figure 15:
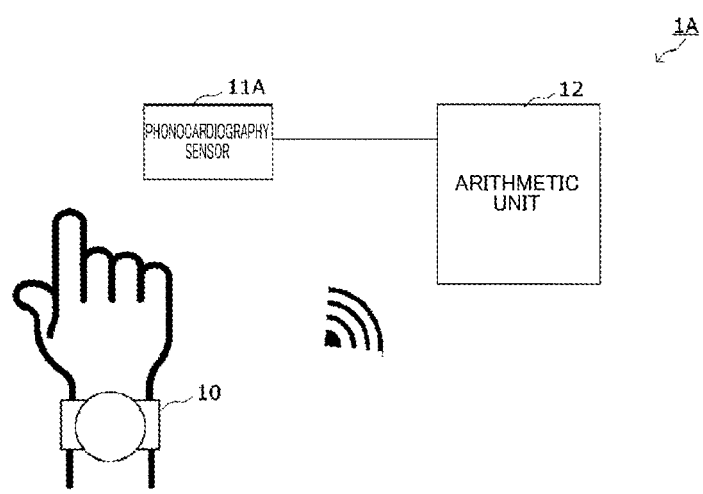
FIG. 15 is a block diagram showing the configuration of an optical blood pressure monitor according to a second embodiment.

FIG. 15 is a block diagram showing the outline of an optical blood pressure monitor 1A according to the present embodiment. The optical blood pressure monitor 1A includes a wristband-type optical sensor device 10, a phonocardiography sensor 11A, and an arithmetic unit 12.

Configuration of Optical Sensor Device

Figure 16:
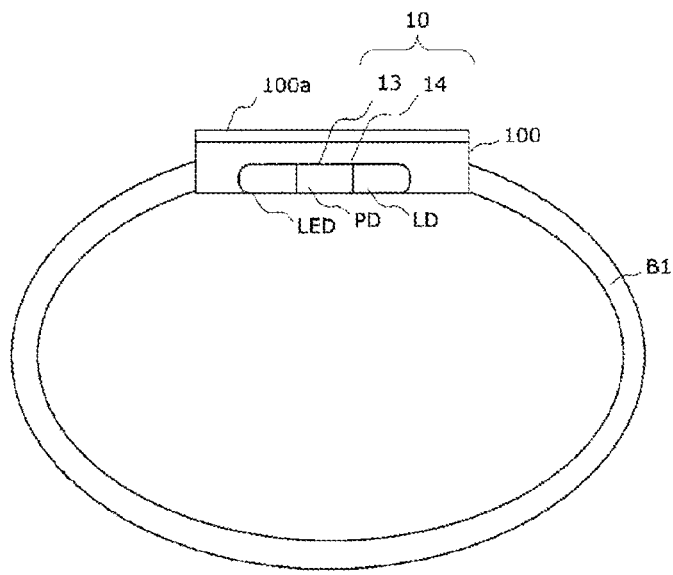
FIG. 16 is a schematic view of an optical sensor device according to the second embodiment as viewed from a side.

The optical sensor device 10 may be provided in a wristband-type wearable terminal such as a smartwatch. FIG. 16 is a schematic view of the optical sensor device 10 as viewed from a side. As shown in FIG. 16, the optical sensor device 10 is provided in a main body 100 to be attached to a user's wrist. The main body 100 may be fixed to the user's wrist by a band B1.

The main body 100 includes a display 100a. The optical sensor device 10 is provided on the back side of the main body 100 that is closer to the wrist and opposite to the surface including the display 100a.

The optical sensor device 10 is configured in a similar manner as the first embodiment, and the laser Doppler blood flowmeter 13 and the photoplethysmography monitor 14 are integrally formed. That is, the optical sensor device 10 includes the LED 40, PDs (PD 31 and PD 41), and LD 30 as sensor elements.

In the present embodiment, the LD 30 of the laser Doppler blood flowmeter 13 emits a laser beam having an infrared wavelength. The LED 40 of the photoplethysmography monitor 14 emits light having an infrared wavelength. Since the optical sensor device 10 of the present embodiment is placed on a wrist of the user, a reflection photoplethysmography monitor 14 for measuring the light reflected through a living body is used.

The blood flow velocity and the pulse waveform in a peripheral blood vessel measured by the laser Doppler blood flowmeter 13 and the photoplethysmography monitor 14, respectively, are transmitted from the communication I/F 15 to the arithmetic unit 12 via wireless communication such as Bluetooth (registered trademark) or Bluetooth Low Energy.

Configuration of Phonocardiography Sensor

The configuration of the phonocardiography sensor 11A is now described. The phonocardiography sensor 11A includes a photoplethysmography microphone and converts the detected heart sound into an electric signal, for example. The phonocardiography sensor 11A may be attached to the body surface of the user's chest, for example. The phonocardiography sensor 11A also includes a communication I/F and transmits the measured phonocardiographic waveform to the arithmetic unit 12 via wire communication or wireless communication such as Bluetooth (registered trademark) or Bluetooth Low Energy.

The functional portions of the arithmetic unit 12 have the same configurations as those described with reference to FIG. 11.

The characteristic point extraction portion 21 extracts characteristic points relating to a heartbeat from the phonocardiographic waveform measured by the phonocardiography sensor 11A. Specifically, as shown in FIG. 4, the end time of Sound I and the start time of Sound II in the phonocardiographic waveform can be extracted as characteristic points.

Based on the time points corresponding to the characteristic points of the phonocardiographic waveform extracted by the characteristic point extraction portion 21, the first calculation portion 22 calculates the pulse wave velocity in the pulse waveform measured by the photoplethysmography monitor 14.

As explained above, with the optical blood pressure monitor 1A of the second embodiment, the optical sensor device 10 in the wristband-type wearable terminal is attached to the user's wrist to determine the user's blood pressure based on the measured blood flow velocity and pulse waveform in a peripheral blood vessel. In this configuration, the optical blood pressure monitor 1A can still measure blood pressure with high accuracy.

The optical blood pressure monitor 1A according to the second embodiment extracts characteristic points relating to a heartbeat from the phonocardiographic waveform measured by the phonocardiography sensor 11A and calculates the pulse wave velocity from the pulse waveform. In this manner, the optical blood pressure monitor 1A can determine the pulse wave velocity also by using the phonocardiographic waveform.

Third Embodiment

A third embodiment of the present invention is now described. Same reference numerals are given to those configurations that are the same as the corresponding configurations of the first embodiment described above. Such configurations will not be described in detail.

The first embodiment uses the heart rate monitor 11, which measures the electrocardiographic waveform, as the sensor for measuring data relating to the pulsation of the heart. The second embodiment includes the phonocardiography sensor 11A for measuring the phonocardiographic waveform. In contrast, the third embodiment uses a photoplethysmography monitor 11B as the sensor for measuring data relating to the pulsation of the heart.

Figure 17:
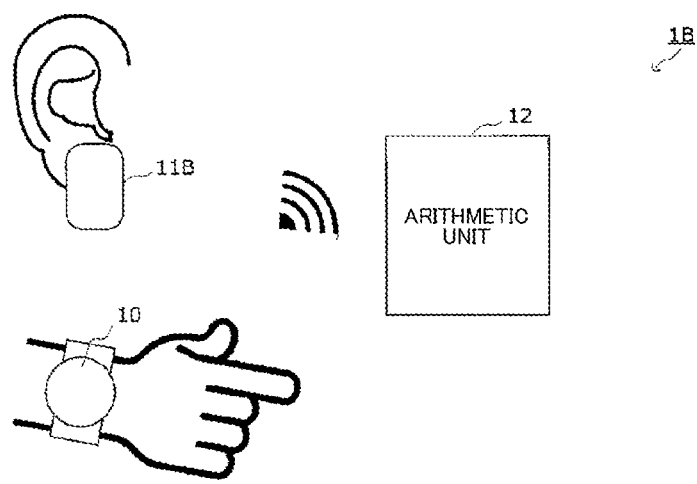
FIG. 17 is a block diagram showing the configuration of an optical blood pressure monitor according to a third embodiment.

FIG. 17 is a block diagram showing the outline of an optical blood pressure monitor 1B according to the present embodiment. The optical blood pressure monitor 1B includes an optical sensor device 10 provided in a wristband-type wearable terminal, a photoplethysmography monitor 11B, and an arithmetic unit 12. The configurations of the optical sensor device 10 and the arithmetic unit 12 are the same as those of the first and second embodiments.

Figure 18:
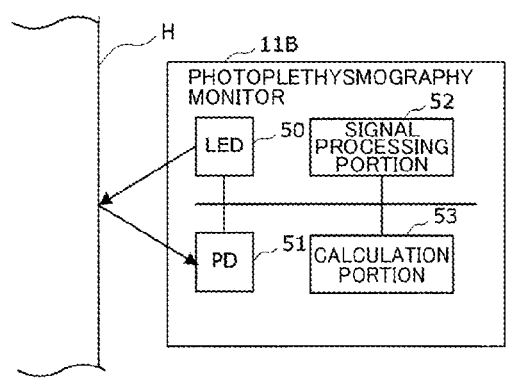
FIG. 18 is a block diagram showing the configuration of a photoplethysmography monitor according to the third embodiment.

FIG. 18 is a block diagram showing the configuration of the photoplethysmography monitor 11B. The photoplethysmography monitor 11B is the same as the photoplethysmography monitor 14 of the optical sensor device 10 described in the first and second embodiments. That is, the photoplethysmography monitor 11B includes a sensor element having an LED 50 and a PD 51. The LED 50 emits incoherent light toward a peripheral blood vessel near the surface of the user's skin. The PD 51 receives reflected light, scattered light, or transmitted light generated when the incoherent light is applied to the blood and converts it into an electric signal by photoelectric conversion.

The photoplethysmography monitor 11B includes a signal processing portion 52, which amplifies, filters, and AD-converts the electric signal output from the PD 51. The photoplethysmography monitor 11B also includes a calculation portion 53, which determines a pulse waveform based on the digital signal obtained by the signal processing portion 52.

As shown in FIG. 17, the photoplethysmography monitor 11B may be placed in a position, such as an earlobe of the user, that is separated from the heart by a given distance and is different from the position of the photoplethysmography monitor 14, which is placed on the user's wrist.

In this case, as shown in FIG. 5, the characteristic point extraction portion 21 compares the pulse waveform measured by the photoplethysmography monitor 11B and the pulse waveform measured by the photoplethysmography monitor 14 provided in the wristband-type wearable terminal to extract a characteristic point as the starting point of the pulse wave transit time. As such, the photoplethysmography monitor 11B, which measures the pulse waveform as data relating to pulsation, and the photoplethysmography monitor 14 in the optical sensor device 10 are placed on the user's body in positions at a certain distance from each other. This increases the accuracy of the calculation of pulse wave velocity.

Additionally, the photoplethysmography monitor 11B includes a communication I/F (not shown) and can transmit the measured pulse waveform to the arithmetic unit 12 by wire communication or wireless communication.

The photoplethysmography monitor 11B may be replaced by the photoplethysmography monitor 14 provided in the wristband-type wearable terminal. In this case, a known algorithm may be applied to the pulse waveform measured by the photoplethysmography monitor 14 to extract a characteristic point from a single pulse waveform.

In such a configuration, the optical blood pressure monitor 1B includes a single photoplethysmography monitor 14, reducing the number of sensors in the optical blood pressure monitor 1B.

As described above, the optical blood pressure monitor 1B of the third embodiment can accurately measure blood pressure using the photoplethysmography monitor 11B as the sensor for measuring data relating to the pulsation of the heart.

In the above-described embodiments, cases in which the optical sensor device 10 is provided in a ring-type and wristband-type wearable terminals are described as specific examples of arrangements. However, the optical sensor device 10 does not have to be placed on a finger or wrist of the user and may be placed on an upper arm of the user, for example.

In this case, the optical sensor device 10 may be provided in a cuff-type wearable terminal. When the optical sensor device 10 is arranged on an upper arm of the user, the laser Doppler blood flowmeter 13 is arranged in contact with an area having a higher capillary density.

Furthermore, the photoplethysmography monitor 11B may be arranged on a toe of the user.

In the embodiments described above, the sensor element including LD 30, LED 40, and PDs (PD 31 and PD 41), the signal processing portions 32 and 42, and the calculation portions 33 and 43 of the laser Doppler blood flowmeter 13 and the photoplethysmography monitor 14 are integrally formed. However, the signal processing portions 32 and 42 and the calculation portions 33 and 43 may be included in the arithmetic unit 12. In this case, the ring member B or the main body 100 of the wristband-type wearable terminal may include only the sensor element.

Additionally, the configurations and the functional portions of the optical blood pressure monitor 1 of the above embodiments may be dispersed on the communication network NW.

The functional blocks, modules, and circuits described in connection with the embodiments disclosed herein may be implemented by general-purpose processors, GPUs, digital signal processors (DSPs), application-specific integrated circuits (ASICs), FPGAs or other programmable logic devices, discrete gate or transistor logic, discrete hardware components, or any combination of the above designed to achieve the functions described above.

Although a microprocessor may be used as a general-purpose processor, it is also possible to use a conventional processor, controller, microcontroller, or other control devices instead of a microprocessor. The processor may also be implemented as a combination of a DSP and a microprocessor, a plurality of microprocessors, one or more microprocessors connected to a DSP core, or a combination of computing devices having such an arbitrary configuration, for example.

The present invention is not limited to a blood pressure monitor of the embodiments of the present invention described above. Various modifications that can be contemplated by those skilled in the art are possible within the scope of the invention described in the claims.

[Reference 1] Crighton Bramwell et al. "The Velocity of the Pulse Wave in Man" Proceedings of the Royal Society of London. Series B, Containing Papers of a Biological Character, Volume 93, Issue 652(1922): 298-306.

REFERENCE SIGNS LIST

1 Optical blood pressure monitor
10 Optical sensor device
11 Heart rate monitor
110 Transmitter
12 Arithmetic unit
13 Laser Doppler blood flowmeter
14 Photoplethysmography monitor
16 Memory
20 Obtainment portion
21 Characteristic point extraction portion
22 First calculation portion
23 Second calculation portion
24 Storage portion
25 Output portion
30 LD
31, 41 PD
32, 42 Signal processing portion
33, 43 Calculation portion
40 LED
W Wearable device
B Ring member
101 Bus
102 Processor
103 Main storage device
15, 104 Communication I/F
105 Auxiliary storage device
106 Input and output I/O
107 Input device
108 Display device

The invention claimed is:

1. An optical blood pressure monitor comprising:
a first measuring instrument configured to measure a blood flow velocity in a peripheral blood vessel without pressurization by a cuff, the first measuring instrument comprising a laser Doppler blood flowmeter configured to be worn on a finger or a wrist of a user;
a second measuring instrument configured to measure a pulse waveform in the peripheral blood vessel without pressurization by the cuff, the second measuring instrument comprising a first photoplethysmography monitor configured to be worn on the finger or the wrist of the user;
a third measuring instrument configured to measure data relating to pulsation of a heart without pressurization by the cuff, wherein the third measuring instrument is an electrocardiograph, a phonocardiography sensor, or a second photoplethysmography monitor configured to be worn on a chest region, an earlobe, or a toe of the user;
a characteristic point extractor configured to extract a characteristic point relating to the pulsation from the data relating to the pulsation of the heart, the characteristic point comprising a time point of an event related to the pulsation;
a first calculator configured to determine a pulse wave velocity from the pulse waveform using a time point of the pulse waveform corresponding to the characteristic point; and
a second calculator configured to determine blood pressure using both the pulse wave velocity and the blood flow velocity.

2. The optical blood pressure monitor according to claim 1, wherein:
in a case in which the third measuring instrument is the electrocardiograph, the data relating to the pulsation of the heart includes an electrocardiographic waveform and the characteristic point comprises a start time point at a junction between two points of the electrocardiographic waveform; and in a case in which the third measuring instrument is the phonocardiography sensor, the data relating to the pulsation of the heart includes a phonocardiographic waveform and the characteristic point comprises a time point corresponding to an end time of a first sound identified on the phonocardiographic waveform or a time point corresponding to a start time of a second sound following the first sound identified on the phonocardiographic waveform.

3. The optical blood pressure monitor according to claim 1, wherein the first measuring instrument comprises:
a first light source configured to emit coherent light toward blood in the peripheral blood vessel; and
a first light receptor configured to receive scattered light generated when the coherent light is applied to the blood and to convert the scattered light into an electric signal, wherein the blood flow velocity is measured based on the electric signal converted by the first light receptor.

4. The optical blood pressure monitor according to claim 1, wherein the second measuring instrument comprises:
a first light source configured to emit incoherent light toward blood in the peripheral blood vessel; and
a first light receptor configured to receive reflected light or transmitted light generated when the incoherent light is applied to the blood and to convert the reflected light or the transmitted light into an electric signal, wherein the pulse waveform is measured based on the electric signal converted by the first light receptor.

5. The optical blood pressure monitor according to claim 1, further comprising a ring member in which the first measuring instrument and the second measuring instrument are provided, wherein the ring member has a tubular shape, and wherein the ring member is configured to be worn on the finger of the user such that the first measuring instrument is disposed on a palmar side of the finger and the second measuring instrument is disposed on a dorsal side of the finger.

6. The optical blood pressure monitor according to claim 1, further comprising:
a main body configured to be affixed to the wrist, wherein the first measuring instrument and the second measuring instrument are provided in the main body; and
a band configured to fix the main body to the wrist.

7. The optical blood pressure monitor according to claim 1, wherein, in a case in which the third measuring instrument is the second photoplethysmography monitor, the second photoplethysmography monitor is configured to be worn by the user at a position separated from the heart by a predefined distance and different from a position of the first photoplethysmography monitor.

8. A method for monitoring a blood pressure using an optical blood pressure monitor, the method comprising:
measuring a blood flow velocity in a peripheral blood vessel without pressurization by a cuff using a laser Doppler blood flowmeter of an optical sensor device worn on a finger or a wrist of a user;
measuring a pulse waveform in the peripheral blood vessel without pressurization by the cuff using a first photoplethysmography monitor of the optical sensor device;
measuring data relating to pulsation of a heart without pressurization by the cuff using an electrocardiograph, a phonocardiography sensor, or a second photoplethysmography monitor worn on a chest of the user, on a toe of the user, or on an ear lobe of the user;
extracting a characteristic point relating to the pulsation from the data relating to the pulsation of the heart, the characteristic point comprising a time point of an event related to the pulsation;
determining a pulse wave velocity from the pulse waveform using a time point of the pulse waveform corresponding to the characteristic point; and
determining the blood pressure using both the pulse wave velocity and the blood flow velocity.

9. The method according to claim 8, wherein:
in a case in which measuring the data relating to the pulsation of the heart is performed using the electrocardiograph, the data relating to the pulsation of the heart includes an electrocardiograph waveform; and
in a case in which measuring the data relating to the pulsation of the heart is performed using the phonocardiography sensor, the data relating to the pulsation of the heart includes a phonocardiographic waveform.

10. The method according to claim 8, wherein the laser Doppler blood flowmeter comprises:
a first light source that emits coherent light toward blood in the peripheral blood vessel; and
a first light receptor that receives scattered light generated when the coherent light is applied to the blood and converts the scattered light into an electric signal, wherein the blood flow velocity is measured based on the electric signal converted by the first light receptor.

11. The method according to claim 10, wherein the first photoplethysmography monitor comprises:
a second light source that emits incoherent light toward the blood in the peripheral blood vessel; and
a second light receptor that receives reflected light or transmitted light generated when the incoherent light is applied to the blood and converts the reflected light or the transmitted light into a second electric signal, wherein the pulse waveform is measured based on the electric signal converted by the second light receptor.

12. The method according to claim 11, further comprising a ring member in which the laser Doppler blood flowmeter and the first photoplethysmography monitor are provided, wherein the ring member has a tubular shape, and wherein the ring member is configured to be worn on the finger of the user such that the laser Doppler blood flowmeter is disposed on a palmar side of the finger and the first photoplethysmography monitor is disposed on a dorsal side of the finger.

13. The method according to claim 8, wherein determining the blood pressure based on the pulse wave velocity and the blood flow velocity comprises calculating a variation amount of the blood pressure ($\Delta P$) using an equation $\Delta P = k \cdot \rho C^2 \cdot (\Delta U/U)$, where k denotes a proportionality constant, $\rho$ denotes blood density, C denotes the pulse wave velocity, U denotes the blood flow velocity, and $\Delta U$ denotes a variation amount of the blood flow velocity.

14. The optical blood pressure monitor according to claim 1, wherein the second calculator is configured to calculate a variation amount of the blood pressure ($\Delta P$) using an equation $\Delta P = k \cdot \rho C^2 \cdot (\Delta U/U)$, where k denotes a proportionality constant, $\rho$ denotes blood density, C denotes the pulse wave velocity, U denotes the blood flow velocity, and $\Delta U$ denotes a variation amount of the blood flow velocity.

15. An optical blood pressure monitor comprising:
a first measuring instrument comprising a laser Doppler blood flowmeter configured to measure a blood flow velocity in a peripheral blood vessel without pressurization by a cuff, wherein the laser Doppler blood flowmeter comprises:

a semiconductor laser configured to emit coherent light toward blood in the peripheral blood vessel; and a first photodiode configured to receive scattered light generated in response to the coherent light being applied to the blood and to convert the scattered light into a first electric signal, wherein the blood flow velocity is measured based on the first electric signal converted by the first photodiode;

a second measuring instrument comprising a photoplethysmography monitor configured to measure a pulse waveform in the peripheral blood vessel without pressurization by the cuff, wherein the laser Doppler blood flowmeter and the photoplethysmography monitor are disposed in a ring member configured to be worn on a finger of a user or are disposed on a main body of a wristband-type wearable terminal configured to be worn on a wrist of the user, and wherein the photoplethysmography monitor comprises:

a light emitting diode configured to emit incoherent light toward the blood in the peripheral blood vessel; and a second photodiode configured to receive reflected light or transmitted light generated in response to the incoherent light being applied to the blood and to convert the reflected light or the transmitted light into a second electric signal, wherein the pulse waveform is measured based on the second electric signal converted by the second photodiode;

a third measuring instrument comprising an electrocardiograph or a phonocardiography sensor configured to measure a heartbeat of the user, wherein the third measuring instrument is configured to be worn near the heart of the user or on an earlobe or a toe of the user;

one or more processors; and a storage device for storing a program to be executed by the one or more processors, the program including instructions to:

extract a characteristic point relating to the heartbeat, the characteristic point comprising a time point of an event related to the heartbeat;

determine a pulse wave velocity from the pulse waveform using a time point of the pulse waveform corresponding to the characteristic point; and determine blood pressure using both the pulse wave velocity and the blood flow velocity.

16. The optical blood pressure monitor according to claim 15, wherein, in a case in which the third measuring instrument comprises the electrocardiograph, the electrocardiograph comprises a shirt-type wearable electrocardiograph device with wearable electrodes configured to be worn on an upper body of the user, a 12-lead electrocardiograph configured to be connected to a chest region of the user, or an electrocardiograph with patch electrodes configured to be connected to the chest region of the user.

17. The optical blood pressure monitor according to claim 15, wherein, in a case in which the third measuring instrument comprises the phonocardiography sensor, the phonocardiography sensor is configured to be attached to a chest region of the user.

* * * * *